(12) United States Patent
Dukat et al.

(10) Patent No.: US 7,301,057 B2
(45) Date of Patent: Nov. 27, 2007

(54) PROCESS FOR PREPARING TCD-ALCOHOL DM

(75) Inventors: Wolfgang Dukat, Oberhausen (DE); Edgar Storm, Oberhausen (DE); Klaus Schmid, Dinslaken (DE)

(73) Assignee: Oxea Deutschland GmbH, Oberhausen (DE)

( * ) Notice: Subject to any disclaimer, the term of this patent is extended or adjusted under 35 U.S.C. 154(b) by 162 days.

(21) Appl. No.: 11/137,761

(22) Filed: May 25, 2005

(65) Prior Publication Data

US 2005/0272960 A1     Dec. 8, 2005

(30) Foreign Application Priority Data

Jun. 8, 2004   (DE) .................... 10 2004 027 955

(51) Int. Cl.
- *C07C 35/23* (2006.01)
- *C07C 35/24* (2006.01)
- *C07C 35/27* (2006.01)
- *C07C 35/37* (2006.01)
- *C07C 35/50* (2006.01)
- *C07C 35/52* (2006.01)

(52) U.S. Cl. .............. 568/817; 568/816; 568/818; 568/822; 568/829; 568/830

(58) Field of Classification Search ............... 568/817, 568/816, 818, 822, 829, 830
See application file for complete search history.

(56) References Cited

FOREIGN PATENT DOCUMENTS

| | | |
|---|---|---|
| DE | 10 30 322 | 5/1958 |
| DE | 10 34 167 | 7/1958 |
| EP | 1 065 194 | 1/2001 |
| GB | 1 170 226 | 11/1969 |

OTHER PUBLICATIONS

Cornils B. et al : "Derivate Des Dicyclopentadiens -Aktuelle Schluesselverbindungen" Chemiker Zeitung, Huethig Verlag, Heidelberg, DE, Bd. 98, Nr. 2, 1974, pp. 70-76, XP-009022594.

*Primary Examiner*—Elvis O. Price
(74) *Attorney, Agent, or Firm*—Charles A. Muserlian

(57) ABSTRACT

The present invention relates to a process for preparing 3(4),8(9)-dihydroxymethyltricyclo[$5.2.1.0^{2.6}$]decane by hydrogenating the hydroformylation products of dicyclopentadiene. The process comprises carrying out the hydrogenation in the presence of water, optionally after addition of water.

13 Claims, No Drawings

PROCESS FOR PREPARING TCD-ALCOHOL DM

The present invention relates to a process for preparing TCD-alcohol DM {3(4),8(9)-dihydroxymethyltricyclo[5.2.1.0$^{2,6}$]decane} from dicyclopentadiene (DCP).

Dicyclopentadiene (DCP), readily available by dimerizing cyclopentadiene and also prepared on the industrial scale, can be converted to compounds having important applications, to which the tricyclodecane structure imparts particular properties. The compounds, derived from DCP, having tricyclodecane structure are frequently named differently in the literature. Based on the nomenclature for DCP derivatives, disclosed by Chemiker-Zeitung, 98, 1974, pages 70 to 76, the nomenclature building on the tricyclodecane structure, also known as TCD structure, is also used hereinbelow.

TCD-Alcohol DM {3(4),8(9)-dihydroxymethyltricyclo[5.2.1.0$^{2,6}$]decane} has great economic significance as an important intermediate for the chemical industry. The dihydric alcohol is versatile and of high industrial interest for different applications: acrylic esters or methacrylic esters of tricyclic decanols containing OH groups (DE 22 00 021), as a constituent of acrylic ester adhesives curing in the absence of oxygen, (meth)acrylic esters of tricyclic decanols containing ether groups (EP 23 686), for preparing adhesives and sealants, esters and polyesters of the tricyclodecane series (DE 934 889) which are suitable as plasticizers and high-value ester lubricants, odorant compositions (DE-B 2 307 627) and polyester varnishes resistant to acid sterilization (DE 31 34 640) in the metal coatings field. TCD-alcohol DM is obtained by hydrogenating the hydroformylation products of dicyclopentadiene, known as the TCD-aldehydes.

The preparation of aldehydes by catalytic addition of carbon monoxide and hydrogen to olefinic double bonds is known. While this reaction has previously been carried out virtually exclusively using cobalt as a catalyst, modern processes work with metallic rhodium or with rhodium compounds as catalysts which are used alone or with complex-forming ligands, for example organic phosphines or esters of phosphorous acid. There is unanimous agreement in the technical field that active catalysts under the reaction conditions are hydridocarbonyl compounds of rhodium which can be expressed by the formula H[Rh(CO)$_{4-x}$L$_x$] where L denotes a ligand and x is 0 or an integer from 1 to 3.

A special case is the hydroformylation of dienes. While the hydroformylation of conjugated dienes under the customary conditions of the oxo process provides almost exclusively monoaldehydes, it is possible to obtain not only the mono- but also the disubstitution products from dicyclopentadiene (DCP) with its isolated double bonds. Owing to the risk of a retro-Diels-Alder reaction at the temperatures of the oxo process and the associated release of Cyclopentadiene which is capable of complex formation with transition metals and can reduce the activity of the catalysts used, the hydroformylation has to proceed under special conditions. It has been found to be advantageous to replace the formerly customary cobalt catalyst with rhodium, which allows a high selectivity of the conversion to aldehydes to be achieved and allows the hydroformylation under conditions under which the extent of retro-Diels-Alder dissociation is lower. A review of the hydroformylation of dicyclopentadiene and of the further processing of the TCD-aldehydes can be found in Chemiker-Zeitung 98, 1974, 70-76. 8(9)-Formyltricyclo[5.2.1.0$^{2,6}$]dec-3-ene, also known as TCD-monenal, and 3(4),8(9)-bisformyltricyclo[5.2.1.0$^{2,6}$]decane, also known as TCD-dialdehyde, are of particular significance. Owing to their thermal lability which leads to losses in distillation, the TCD-aldehydes are usually not isolated in pure form, but rather further processed as crude products of the hydroformylation reaction.

For example, GB 1,170,226 discloses either the hydrogenation of the hydroformylation mixture, obtained under rhodium catalysis, of the dicyclopentadiene hydroformylation after removal of the rhodium catalyst in the presence of a common hydrogenation catalyst, or else the conversion of the reaction mixture to TCD-alcohol DM without removal of the rhodium catalyst and without addition of a further hydrogenation catalyst, at elevated temperature in the presence of synthesis gas.

According to EP-A2-0 348 832, which relates to the preparation of 3(4),8(9)-bis(aminomethyl)tricyclo[5.2.1.0$^{2,6}$]decane (TCD-diamine), the rhodium-containing reaction mixture of the dicyclopentadiene hydroformylation is fed without removal of the catalyst to the subsequent reductive amination, in the course of which the rhodium used in the hydroformylation stage is deposited virtually fully on the hydrogenation catalyst.

As a consequence of the various possible applications, TCD-alcohol DM is of high economic interest and the patent literature contains numerous references to processes for its preparation.

The U.S. Pat. No. 4,647,708 describes the hydroformylation of dicyclopentadiene using Rh as a catalyst in the presence of ion exchangers (Dowex® MWA-1) in toluene/THF as solvents. The reaction is effected at 120° C. and 27.5 MPa of CO/H$_2$ (in a ratio of 1:2) in two separate continuous autoclaves. With reference to the experimental results disclosed, it can be seen that the yield of TCD-alcohol DM falls from 85% to 65% within the 30-day experimental period. The reaction system is thus unsuitable for industrial use.

U.S. Pat. No. 4,262,147 describes the use of bimetallic Rh/Co clusters on resins such as Amberlite® IRA-68. Under the conditions employed (110° C., 11 MPa, 8 hours), a selectivity of 68% of TCD-alcohol DM is obtained in this one-stage synthesis.

A modified Co process is described in DE-C 3 008 497, where dicyclopentadiene is converted under Co/tri-n-octylphosphine catalysis at 200° C. and a synthesis gas pressure of 15 MPa. After a reaction time of 5 hours, the TCD-alcohol DM is obtained in a yield of 69%. The by-products formed are 11.7% of the TCD-monoalcohol and 14.6% of hydroxymethylcyclopentane. Owing to the high temperatures which are necessarily employed, there is retro-Diels-Alder reaction of dicyclopentadiene to cyclopentadiene and thus the formation of significant amounts of hydroxymethylcyclopentane. This process variant is therefore unsuitable for industrial application.

JP 111 00 339 discloses the performance of the hydroformylation of DCP in isopropanol/toluene using rhodium dicarbonyl acetylacetonate, tris(2,4-di-tert-butylphenyl)phosphite and triethylamine at 120° C. under 8.8 MPa of synthesis gas over 8 hours. 93% of TCD-dialdehyde is obtained and is hydrogenated in isopropanol at 110° C. and 0.78 MPa of hydrogen for 6 hours over Raney nickel to give 91% of TCD-alcohol DM. The use of the complex phosphite ligands which are difficult to prepare is disadvantageous for industrial application and also for economic reasons. In addition, the broad use of phosphite ligands is restricted by their low stability and higher hydrolysis sensitivity toward water and acid traces compared to conventional phosphine ligands, and the phosphonous acids formed during the continuous hydroformylation process impair the catalyst lifetime and have to be removed from the process in a complicated manner. Moreover, when amines are used, contamination of the TCD-alcohol DM with nitrogen-containing components is always to be expected.

EP 1 065 194 describes a low-pressure process for hydroformylating dicyclopentadiene, in which the catalyst system used is likewise Rh/tris(2,4-di-tert-butylphenyl) phosphite. The hydroformylation is carried out at pressures of 1-15 MPa and temperatures of 80-140° C. The solvents used are inert hydrocarbons such as toluene, diisopropylbenzene or methylcyclohexane. The hydroformylation product is worked up by a multistage extraction using polyhydric alcohols, for example ethylene glycol, and the addition of tertiary amines is recommended. After the extraction, the crude oxo product is present predominantly in the alcohol phase, while small proportions of mono- and dialdehyde, and also the majority of rhodium and phosphine ligands, are in the hydrocarbon phase. It is pointed out that the extraction has to be effected in the absolute absence of oxygen. The use of extractants with addition of tertiary amines, and also the absolute necessity of the absence of oxygen complicate the industrial performance of this process and include the risk of contamination of TCD-alcohol DM with traces of amines.

The known processes for preparing TCD-alcohol DM by hydroformylating dicyclopentadiene with subsequent hydrogenation entail either the presence of specific catalyst systems which are unavailable in industry or environmentally incompatible, or enable only economically unsatisfactory selectivities and yields of TCD-alcohol DM. There is therefore a need for a very simple and inexpensive process for preparing TCD-alcohol DM.

The invention therefore consists in a process for preparing 3(4),8(9)-dihydroxymethyltricyclo[5.2.1.0$^{2,6}$]decane by hydrogenating the hydroformylation products of dicyclopentadiene. It comprises carrying out the hydrogenation in the presence of water, optionally after addition of water.

It has been found that, surprisingly, the presence of water in the hydrogenation stage leads to a distinct improvement in the yield of TCD-alcohol DM. Water may be present directly in the crude hydroformylation product, used in the hydrogenation stage, of the dicyclopentadiene hydroformylation, or else water may be added to the crude hydroformylation product before or during the hydrogenation stage.

The hydroformylation of dicyclopentadiene is carried out generally in homogeneous organic phase in the presence of rhodium catalysts which are soluble in the organic reaction mixture. One way of carrying out the hydroformylation reaction is by conventional processes in the absence of water. However, it is also possible to add water to the homogeneous hydroformylation mixture. When water is added to the organic phase, the amount of water used is generally determined by the water solubility in the organic reaction mixture. However, the addition of water to the reaction mixture in an amount over and above the solubility limit is not ruled out.

The water addition is generally at least 0.1% by weight, preferably at least 0.5% by weight, based in each case on the total use.

When water is added to the reaction mixture over and above the solubility limit, it is advantageous before carrying out the hydroformylation stage to remove separated water, preferably via a phase separation.

The hydroformylation stage is carried out generally in a homogeneous reaction system. The term homogeneous reaction system represents a homogeneous solution composed substantially of solvent, if added, catalyst, starting materials, reaction product and added water. In some cases, a solvent addition may be found to be appropriate. The solvents used are organic compounds in which starting material, reaction product and catalyst system are soluble. Examples of such compounds are aromatic hydrocarbons such as benzene and toluene or the isomeric xylenes and mesitylene. Other useful solvents are paraffin oil, cyclic, straight-chain or branched hydrocarbons such as cyclohexane, n-hexane, n-heptane or n-octane, ethers such as tetrahydrofuran, ketones or Texanol® from Eastman. It is possible to add to the solvent further diluents such as aliphatic alcohols, for example 2-ethylhexanol or isobutanol. The fraction of the solvent in the reaction medium may be varied over a wide range and is typically between 10 and 90% by weight, preferably from 20 to 50% by weight, based on the reaction mixture.

A solvent addition in the hydroformylation stage is, however, not necessarily required.

If water is added to the organic hydroformylation mixture, the amount of water is advantageously such that, after addition of water, a homogeneous liquid organic phase is still present and no separate water phase separates. The solubility limit of water in the organic reaction mixture depends upon various influences, for example on the polarity of the solvent used and its fraction in the reaction mixture, and can be determined by simple experiments. Water additions of less than 0.1% by weight, based on the total amount used, no longer bring about any advantageous effect and are therefore dispensible and unnecessarily complicate the reaction.

It is likewise possible to add water in the hydroformylation stage in such an amount that a separate water phase forms. However, in this process variant too, in which a heterogeneous mixture of water and organic phase is used in the hydroformylation stage, the hydroformylation catalyst remains dissolved in the organic phase.

When aliphatic or aromatic hydrocarbons such as toluene or cyclohexane are used as solvents, the water content in a preferred embodiment of the process according to the invention is from 0.5 to 2.5% by weight, preferably from 1.0 to 2.0% by weight, based on the total use.

The catalysts used in the hydroformylation stage are rhodium compounds. The rhodium compounds used are generally not modified with phosphorus ligands such as phosphines or phosphites. Such rhodium catalysts not modified with phosphines or phosphites and their suitability as a catalyst for hydroformylation are disclosed by the literature and they are referred to as unmodified rhodium catalysts. The technical literature assumes that the rhodium compound $HRh(CO)_4$ is the catalytically active rhodium species in the hydroformylation with unmodified rhodium catalysts, even though this has not been proved unambiguously as a consequence of the many chemisms proceeding in parallel in the hydroformylation zone. Since the use of rhodium catalysts not modified with phosphines generally entails a relatively low rhodium content, preference is given to working in the hydroformylation stage with unmodified rhodium catalysts. The rhodium content is generally from 5 to 100 ppm, based on the homogeneous reaction mixture.

However, it is also possible in the hydroformylation stage to use rhodium complexes which contain organic phosphorus(III) compounds as ligands. Such complexes and their preparation are known (for example from U.S. Pat. No. 3,527,809, U.S. Pat. No. 4,148,830, U.S. Pat. No. 4,247,486, U.S. Pat. No. 4,283,562). They may be used in the form of single complexes or else in the form of a mixture of different complexes. The rhodium concentration in the reaction medium extends over a range of from about 5 to about 1000 ppm by weight and is preferably from 10 to 700 ppm by weight. In particular, rhodium is used in concentrations of from 20 to 500 ppm by weight, based in each case on the homogeneous reaction mixture. The catalyst used may be the rhodium complex having a stoichiometric composition. However, it has been found to be appropriate to carry out the hydroformylation in the presence of a catalyst system composed of rhodium-phosphorus complex and free, i.e. excess, phosphorus ligand which does not enter into complexation with rhodium. The free phosphorus ligand may be the same as in the rhodium complex, but it is also possible to use ligands different therefrom. The free ligand may be a single compound or consist of a mixture of different organophosphorus compounds. Examples of rhodium-phosphorus complexes which may find use as catalysts are described in U.S. Pat. No. 3,527,809. The preferred ligands in the rhodium complex catalysts include, for example, triarylphosphines such as triphenylphosphine, trialkylphosphines such as tri(n-octyl)phosphine, trilaurylphosphine, tri(cyclohexyl)phosphine, alkylphenylphosphines, cycloalkylphenylphosphines and organic diphosphites. Owing to its ease of obtainability, triphenylphosphine is employed particularly frequently.

When operation is effected with a modified rhodium complex catalyst system, the molar ratio of rhodium to phosphorus in the homogeneous reaction mixture is typically from 1:5 to 1:200, but the molar proportion of phosphorus in the form of organic phosphorus compounds may also be higher. Preference is given to using rhodium and organically bonded phosphorus in molar ratios of from 1:10 to 1:100.

The hydroformylation of dicyclopentadiene with carbon monoxide and hydrogen is effected at temperatures of from 70 to 150° C. Preference is given to maintaining temperatures of from 80 to 140° C. and in particular from 100 to 140° C. The total pressure extends over a range of from 5 to 35 MPa, preferably from 10 to 30 MPa and in particular from 20 to 30 MPa. The molar ratio of hydrogen to carbon monoxide varies typically between 1:10 and 10:1; mixtures which contain hydrogen and carbon monoxide in a molar ratio of from 3:1 to 1:3, in particular about 1:1, are particularly suitable.

The catalyst is typically formed from the components of transition metal or transition metal compound and synthesis gas under the conditions of the hydroformylation reaction in the reaction mixture, optionally in the presence of organic phosphorus(III) compounds. However, it is also possible to initially preform the catalyst and subsequently feed it to the actual hydroformylation stage. The conditions of the preformation generally correspond to the hydroformylation conditions.

To prepare the hydroformylation catalyst, rhodium is used either in metallic form or as a compound. In metallic form, rhodium is used either in the form of finely divided particles or precipitated in a thin film on a support such as activated carbon, calcium carbonate, aluminum silicate, clay earth. Suitable rhodium compounds are salts of aliphatic mono- and polycarboxylic acids, such as rhodium 2-ethylhexanoate, acetate, oxalate, propionate or malonate. In addition, salts of inorganic hydrogen and oxygen acids may be used, such as nitrates or sulfates, the different transition metal oxides or else transition metal carbonyl compounds such as $Rh_3(CO)_{12}$, $Rh_6(CO)_{16}$, or transition metal complexes, for example cyclopentadienyl-rhodium compounds, rhodium acetylacetonate or [RhCl(cyclooctadiene-1,5)]2. Owing to the corrosive behavior of the halide ions, rhodium-halogen compounds are less useful.

It has been found that rhodium oxide, rhodium acetate and rhodium 2-ethylhexanoate are particularly suitable.

The hydroformylation stage may be carried out either batchwise or continuously.

The reaction products of the dicyclopentadiene hydroformylation are fed to the hydrogenation stage without further purification, without catalyst removal and without solvent removal if solvent has been added. There is no removal of the water present and/or added beforehand in the hydroformylation stage.

If water is added in the hydroformylation stage in such an amount that its solubility in the organic phase is exceeded, the water phase which separates can be removed by means of phase separation before entry into the hydrogenation reactor. However, it is also possible to use a heterogeneous mixture of water and organic phase in the hydrogenation stage.

However, a water addition in the hydroformylation stage carried out in homogeneous phase using rhodium catalysts which are soluble homogeneously in the organic reaction mixture is not necessarily required. In this case, dicyclopentadiene is initially hydroformylated in the homogeneous reaction medium by conventional processes.

In the process according to the invention, the hydrogenation of the hydroformylation products of dicyclopentadiene is carried out in the presence of, optionally after addition of, water. The water may be added before or during the hydrogenation to TCD-alcohol DM.

Since the crude TCD-dialdehyde used has a higher polarity in comparison to the dicyclopentadiene, the solubility limit of the water added in the reaction mixture increases and water can be added in a higher amount without a separate water phase separating. Water additions below 0.1% by weight, based on the total use amount, bring about no technical advantage. Preference is given to adding water to the reaction mixture to a content of from 0.5 to 5.0% by weight, in particular from 1.0 to 4.0% by weight, based on the total use amount.

However, it is likewise possible to add water to the reaction mixture resulting from the hydroformylation stage over and above the solubility limit.

The hydrogenation of the crude TCD-dialdehyde to TCD-alcohol DM is effected under generally customary reaction conditions in the presence of conventional hydrogenation catalysts. In general, the hydrogenation temperature is from 70 to 170° C. and the pressure employed from 1 to 30 MPa. Suitable hydrogenation catalysts are particularly nickel catalysts.

The catalytically active metal may be applied to a support, generally in an amount of from about 5 to about 70% by weight, preferably from about 10 to about 65% by weight and in particular from about 20 to about 60% by weight, based in each case on the total weight of the catalyst. Suitable catalyst supports are all conventional support materials, for example alumina, alumina hydrates in their various manifestations, silicon dioxide, polysilicas (silica gels) including kieselguhr, silica xerogels, magnesium oxide, zinc oxide, zirconium oxide and activated carbon. In addition to the main components, nickel and support material, the catalysts may also comprise additives in minor amounts which serve, for example, to improve their hydrogenation activity and/or their lifetime and/or their selectivity. Such additives are known; they include, for example, the oxides of sodium, potassium, magnesium, calcium, barium, zinc, aluminum, zirconium and chromium. They are added to the catalysts generally in a total proportion of from 0.1 to 50 parts by weight, based on 100 parts by weight of nickel.

However, unsupported catalysts such as Raney nickel or Raney cobalt may also be used in the hydrogenation process.

The hydrogenation stage is carried out batchwise or continuously in the liquid phase using suspended catalysts, or in the liquid or gaseous phase using fixed bed catalysts; preference is given to the continuous procedure.

In a batchwise process, based on TCD-dialdehyde, from 1 to 10%, preferably from 2 to 6% by weight, of nickel in the form of the above-described catalysts is used. In a continuous procedure, from about 0.05 to about 5.0 kg of the TCD-dialdehyde are used per liter of catalyst and hour; preference is given to from about 0.1 to 2.0 kg of TCD-dialdehyde per liter of catalyst and hour.

The hydrogenation is preferably effected using pure hydrogen. However, it is also possible to use mixtures which comprise free hydrogen and additionally constituents inert under the hydrogenation conditions. In any case, care has to be taken that the hydrogenation gas is free of catalyst poisons such as sulfur compounds or carbon monoxide in harmful amounts.

The rhodium from the unremoved hydroformylation catalyst precipitates virtually fully on the hydrogenation catalyst. It can be recovered by known processes.

It is recommended to use solvents or diluents in the hydrogenation stage, which may be pure substances or else substance mixtures. Examples of suitable solvents or diluents are linear or cyclic ethers such as tetrahydrofuran or dioxane, and also aliphatic alcohols such as methanol, 2-ethylhexanol or isobutanol. The amount of the solvent or diluent used may be selected freely in accordance with the circumstances of the apparatus and process; in general, solutions are used which contain from 10 to 75% by weight of TCD-dialdehyde. It has been found to be particularly useful in the process according to the invention to use the diluent present from the hydroformylation stage as a solvent or diluent. In this case, based on the weight of the TCD-dialdehyde, appropriately from 1 to 10 times, preferably from 1 to 5 times, the amount of the solvent and diluent is present or is added.

The pure TCD-alcohol DM is recovered by conventional distillation processes. Residual amounts of the rhodium used in the hydroformylation stage are obtained in the distillation residue and are recovered by known processes.

The process according to the invention is illustrated in detail hereinbelow with reference to some examples, but it is not restricted to the embodiments described.

Comparative Experiment

Dicyclopentadiene was hydroformylated by the process known from GB-1,170,226 under rhodium catalysis in the presence of toluene. A 65% by weight toluenic solution of dicyclopentadiene was converted at a temperature of 130° C. and a pressure of 26 MPa in the presence of 20 ppm of rhodium.

Subsequently, the crude product was hydrogenated over a fixed bed nickel catalyst at a temperature of 120° C. and a pressure of 10.0 MPa and subsequently distilled.

The yield of TCD-alcohol DM was 70.5% based on dicyclopentadiene used.

EXAMPLE 1

The procedure was analogous to Example 1 with the single exception that 1.60% by weight of water, based on the use mixture, had been added to the use mixture for dicyclopentadiene hydroformylation.

The crude product obtained after the hydroformylation was hydrogenated analogously to the comparative experiment without further purification and subsequently distilled.

The yield of TCD-alcohol DM was 80.3% based on dicyclopentadiene used.

Surprisingly, it is possible to convert aqueous hydroformylation products of dicyclopentadiene hydroformylation or hydroformylation mixtures after water addition to TCD-alcohol DM in the subsequent hydrogenation stage with excellent yields.

What is claimed is:

1. A process for preparing 3(4), 8(9)-dihydroxymethyltricyclo[5.2.1$0^{2,6}$]-decane comprising hydrogenating the hydroformylation products of dicyclopentadiene in the presence of water, optionally after addition of water, whereas the hydroformylation products of dicyclopentadiene are fed to the hydrogenation stage without further purification and without catalyst removal.

2. The process of claim 1, wherein the water is added before or during hydrogenation.

3. The process of claim 1, wherein water is added to the reaction mixture in the hydrogenation to a content of from 0.5 to 5.0% by weight, based on the total use amount.

4. The process of claim 1, wherein the hydrogenation is effected in the presence of aliphatic alcohols.

5. The process of claim 1, wherein the hydrogenation is carried out in the presence of nickel catalysts.

6. The process of claim 1, wherein the hydrogenation is carried out at a temperature of from 70 to 170° C. and at a pressure of from 1 to 30 MPa.

7. The process of claim 1, wherein the hydroformylation products of dicycylopentadiene are obtained by hydroformylation in homogeneous organic phase in the presence of homogeneously dissolved rhodium catalysts.

8. The process of claim 7, wherein the hydroformylation is effected in the presence of water.

9. The process of claim 8, wherein water is present in an amount of at least 0.1% by weight, based on the total use.

10. The process of claim 9, wherein the water content is from 0.5 to 2.5% by weight, based on the total use.

11. The process of claim 9 wherein the water content is 1.0 to 2.0% by weight.

12. The process of claim 3 wherein the water is added to a content of 1.0 to 4.0% by weight.

13. The process of claim 10 wherein the amount of water is at least 0.5 by weight.

* * * * *